United States Patent
Choay et al.

(10) Patent No.: US 6,610,543 B2
(45) Date of Patent: Aug. 26, 2003

(54) CELLULAR CULTURE MEDIUM, PARTICULARLY FOR IN VITRO FERTILIZATION, OR FOR THE CULTURE OF FOLLICLES, MALE GERM CELLS OR EMBRYOS

(75) Inventors: Patrick Choay, Paris (FR); Serge Weinman, Paris (FR)

(73) Assignee: Laboratoire C.C.D., Paris (FR)

( * ) Notice: Subject to any disclaimer, the term of this patent is extended or adjusted under 35 U.S.C. 154(b) by 0 days.

(21) Appl. No.: 09/910,758

(22) Filed: Jul. 24, 2001

(65) Prior Publication Data

US 2002/0028509 A1 Mar. 7, 2002

(30) Foreign Application Priority Data

Jul. 24, 2000 (FR) ............................................. 00 09694

(51) Int. Cl.[7] ............................... C12N 5/08; C12N 5/06
(52) U.S. Cl. ........................ 435/384; 435/366; 435/325; 435/405; 435/385
(58) Field of Search ................................ 435/366, 325, 435/405, 384, 385

(56) References Cited

U.S. PATENT DOCUMENTS 5,712,163 A * 1/1998 Parenteau et al. .......... 435/405
6,110,741 A * 8/2000 Hearn ........................ 435/363
2001/0033835 A1 * 10/2001 Daley et al. ............. 424/92.21

FOREIGN PATENT DOCUMENTS

WO WO 96/12793 5/1996

OTHER PUBLICATIONS

Lim et al., Roles of growth factors in the development of bovine embryos fertilized in vitro and cultured singly in a defined medium, 1996, Reprod. Fertil. Dev., vol. 8, pp. 1199–1205.*

Invitrogen/Tech–On–Line/, www.lifetech.com. TPN (triphosphopyridine nucleotide–Na).*

D.T. Loo et al. "Differentiation of Serum–Free Mouse Embryo Cells Into Astrocytes Is Accompanied by Induction of Glutamine Synthetase Activity", Journal of Neuroscience Research, 42, 1995, pp. 184–191.

Shyamal K. Roy, "Epidermal Growth Factor and Transforming Growth Factor—β Modulation of Follicle–Stimulating Hormone–Induced Deoxyribonucleic Acid Synthesis in Hamster Preantral and Early Antral Follicles", Biology of Reproduction, 48, 1993, pp. 552–557.

* cited by examiner

Primary Examiner—Anne-Marie Falk
Assistant Examiner—Daniel M Sullivan
(74) Attorney, Agent, or Firm—Young & Thompson

(57) ABSTRACT

The invention relates to compositions for in vitro fertilization, or for the in vitro culture of follicles, male germinal cells or embryos, said compositions comprising at least two growth factors in association with a compound of the family of corticoids involved in energetic production in mammals. The invention also relates to the culture media obtained with these compositions, these latter being preferably in the form of a lyophilizate. The invention also has for its object processes for the in vitro fertilization and processes for maturation of follicles, of male germinal cells, or embryos using such culture media, as well as kits for the practice of these processes and comprising a lyophilizate as mentioned above and an aqueous solution, if desired commercial, containing other constituents of said culture medium.

13 Claims, No Drawings

CELLULAR CULTURE MEDIUM, PARTICULARLY FOR IN VITRO FERTILIZATION, OR FOR THE CULTURE OF FOLLICLES, MALE GERM CELLS OR EMBRYOS

BACKGROUND OF HE INVENTION

1. Field of the Invention

The present invention has for its object compositions useful as cellular culture media, particularly for follicles in the course of development or for the maturation of cells of the male germinal line, as well as for the in vitro fertilization and development of embryos, and more particularly mammal embryos, particularly human embryos, if desired frozen.

2. Description of the Related Art

After maturation of the De Graaf follicle, ovulation permits the oocyte to pass into the Fallopian tube there possibly to be fertilized. The resulting embryo stays there 3 to 5 days for development and reaches the stages of morula, and then blastocyte.

In the tubes, the gametes, the embryo, the morula, then the blastocyte are surrounded by tube fluid. The composition of this latter is complex: it associates fundamental components of the internal medium of the mother with those of the follicle liquid, and it does not seem to undergo great qualitative changes in the course of the first days of the first phase of the post-ovulatory phase. Reaching the blastocyte stage, the embryo passes into the uterus whose mucosa have thus reached a stage of development favorable for the implantation and nidation of the egg.

The passage of the embryo into the uterus does not take place until one and the other have arrived at the level of physiological development compatible with the implantation and nidation: the blastocyte stage for the embryo, the endometrium near its secretory phase for the uterus.

In the case of medically assisted conception, these physiological conditions suggest a single and constant culture medium, and not sequential ones as actually exists, associating all the elements necessary for the development, the in vitro fertilization, and if desired subsequent to ICSI (intra cytoplasmic sperm injection, or intracytoplasmic injection of spermatozoa), until transfer of the embryo.

SUMMARY OF THE INVENTION

The present invention results from the discovery by the inventors of constant compositions usable as well for follicle cultures as for cells of the male germinal line, and also for fertilization of the oocyte and the development of the embryo, until th blastocyte stage, and this with comparable yields, or even greater yields than those obtained with compositions now on the market.

The present invention has for its object compositions for the in vitro culture of cells, characterized in that they comprise at least two growth factors (hereinafter called GF) such as recombinant human growth factors, preferably in association with at least one compound of the corticoid family involved in the production of energy in mammals, and more particularly of the glucocorticoid family, such as hydrocortisone or a derivative of the same family, preferably in water soluble form, and, as the case may be, in association with at least one key co-enzyme of energy metabolism, such as NAD/NADH and NADP/NADPH.

DETAILED DESCRIPTION OF THE PREFERRED EMBODIMENTS

More particularly, the invention has for its object the above-mentioned compositions for the in vitro culture of follicles in the course of development for maturation of the oocytes contained in said follicles, or for the maturation of cells of the male germinal line, or for the in vitro fertilization of oocytes by spermatozoa, or for the culture of embryos, if desired after thawing the follicles, male cells or embryos.

Preferably, the grown factors contained in the compositions of he invention belong to five families of cytokines. The hormones and the growth factors are present in equilibrium concentrations, compatible with physiological conditions. The compositions of the invention bring to the growing and differentiating cells the regulatory molecules which they must have. Thus, these compositions are adapted to permit the maturation of immature human oocytes cultivated in the presence of follicle cells, as well as the maturation of the cells of the mal germinal line. They can also ensure the development of the human embryo to the blastocyte stage. However, this stag has a higher percentage of implantation in the uterus than when the transfer of the embryo takes place at a less advanced stage, particularly at the stages of two to about eight cells.

The invention more particularly has for its object the above mentioned compositions, comprising at least two growth factors, selected from:

the hepatic growth factor, also called HGF (hepatocyte growth factor), the transformation growth factor $\alpha$, also called TGF$\alpha$ (transforming growth factor), the factor for stimulating colonies of granulocytes and macrophages, also called GM-CSF (granulocyte-macrophage colony stimulating factor), the epidermal growth factor, also called EGF and/or HB-EGF (heparin-binding epidermal growth factor), the growth and differentiation factors, also called GDF, such as GDF-9, the insulin-like growth factors, such as IGF-1 and/or IGF-2.

Preferably, the compositions of the invention contain at least three growth factors selected from those listed above.

Particularly preferred compositions contain at least IGF-1 and/or IGF-2.

Also preferably, the above-mentioned compositions of the invention comprise all the above-mentioned growth factors.

Preferably, the concentrations of the growth and differentiation factors in the above-mentioned compositions of the invention are nanomolecular, and preferably comprise between about 0.25 µg/L and about 60 µg/L, particularly between about 0.5 µg/L and about 50 µg/L.

Preferably, the concentrations of the growth and differentiation factors contained in the compositions of the invention are such that:

the concentration of EGF is about 40 µg/L to about 60 µg/L, particularly about 50 µg/L, the concentration of TGF$\alpha$ is about 20 µg/L to about 30 µg/l, particularly about 25 µg/L, the concentration of HGF is about 40 µg/L to about 60 µg/L, particularly about 50 µg/L, the concentration of GM-CSF is about 1.25 µg/L to about 1.75 µg/L, particularly about 1.5 µg/L, the concentration of GDF-9 is about 4 µg/L to about 6 µg/L, particularly about 5 µg/L, the concentration of IGF-1 is about 12.5 µg/L to about 17.5 µg/L, particularly about 15 µg/L, the concentration of IGF-2 is about 12.5 µg/L to about 17.5 µg/L, particularly about 15 µg/L.

The invention also has for its object the above-mentioned compositions for in vitro culture, comprising a compound of the family of corticoids such as those defined above, and preferably hydrocortisone.

Preferably, the above-mentioned hydrocortisone is present in the form of a hydrosoluble salt, particularly in the form of hydrocortisone hemisuccinate. Preferably, the concentration of the hydrocortisone salt in the above-mentioned compositions, is comprised between about $5\times10^{-7}$ M and about $10^{-6}$ M, and is particularly about $7\times10^{-7}$ M, or about 350 µg/L for hydrocortisone hemisuccinate.

Preferably, the compositions defined above contain key co-enzymes of the energetic metabolism mentioned above, particularly at concentrations such that:

the concentration of NAD/NADH will be about 1 mg/L,
the concentration of NADP/NADPH will be about 1 mg/L.

The invention also relates to the compositions defined above present in the form of the lyophilisate, namely in the form of compositions whose different constituents are brought to the dry condition, and are adapted to be returned to solution keeping their physico-chemical and biological properties.

In this connection, the invention more particularly has for its object the above-mentioned lyophilisates, containing:

at least two growth factors as defined above, or all of these factors,
at least one compound of the family of corticoids defined above, such as hydrocortisone hemisuccinate,
and, as the case may be, at least one key co-enzyme of the energetic metabolism defined above, such as NAD/NADH and NADP/NADPH.

The invention also has for its object the use of the above-mentioned compositions or lyophilisates, as adjuvants effective for the preparation of in vitro culture media of follicles in the course of development for the maturation of the oocytes contained in said follicles, or for the maturation of cells of the male germinal line, or for the in vitro fertilization of oocytes by spermatozoa, or for the embryonic culture, if desired after thawing the follicles, male cells or embryos, said in vitro culture media comprising a composition as defined above, in association with elements used conventionally in in vitro fertilization, or for the culture of follicles, male cells or embryos, said elements being selected particularly from human or bovine albumin serum, as the case may be recombinant, and/or the mineral salts, and/or the energetic molecules such as glucose, pyruvate and lactate, and/or the amino acids for the biosynthesis of proteins, and/or the purine and pyrimidine bases for the biosynthesis of nucleic acids, and/or phospholipids or cholesterol for he formation of cellular membranes, and/or vitamins, such as vitamins of the B group, particularly vitamin B5 (pantothenate), vitamin B8 (biotin), vitamin B1 (thiamin) and/or vitamin C.

The invention also relates to a process for the production of in vitro culture media defined above, characterized in that it comprises a step of mixing a composition as defined above, as the case may be after dissolution in a suitable volume of an above-mentioned composition in the form of a lyophilisate, with a solution containing the elements conventionally used in the field of in vitro fertilization, or follicle culture, male cell or embryo culture, said elements being as defined above.

The invention more particularly has for its object the in vitro culture media for follicles in the course of development for the maturation of the oocytes contained in said follicles, or for the maturation of cells of the male germinal line, or for the in vitro fertilization of oocytes by spermatozoa, or for the culture of embryos, if desired after thawing the follicles, male cells or embryos, said media being as obtained by practice of an above-mentioned process, and being characterized in that they comprise a composition as defined above, in association with the above-mentioned elements conventionally used in the field of in vitro fertilization, or follicle culture, male cell or embryo culture.

The invention also relates to a process for the development of mammal embryos, and more particularly human embryos, as the case may be after thawing previously frozen embryos, characterized in that it comprises a step of in vitro culturation of said embryos, in a culture medium such as defined above according to the invention, preferably for the six first days after in vitro fertilization, as the case may be after thawing, preferably so as to obtain embryos in the blastocyte stage.

The invention also has for its object a process for the maturation of mammal follicles in the course of development for the maturation of the oocytes contained in said follicles, and more particularly human follicles, as the case may be after thawing of previously frozen follicles, characterized in that it comprises a step of in vitro culturation of follicles from the female, and more particularly from a woman, in a culture medium as defined above according to the invention, preferably for about 3 days to about 6 days.

The invention also relates to a process for maturation of cells of the male germinal line of mammals, and more particularly humans, as the case may be after thawing previously frozen cells, characterized in that it comprises a step of in vitro culturation of said cells, in a culture medium as defined above according to the invention, preferably for about 3 days to about 5 days.

The invention also has for its object a process of in vitro fertilization of oocytes by spermatozoa, and more particularly of oocytes and spermatozoa of human origin, as the case may be after thawing previously frozen spermatozoa, characterized in hat it comprises a step of in vitro culturation of the oocytes a d spermatozoa mentioned above, in a culture medium as define above according to the invention, preferably for about 2 days to about 6 days.

Preferably, the compositions of the invention can be used both for the maturation of oocytes or of cells of the male germinal line, th in vitro fertilization of the oocytes, and the maturation of the embryos from said fertilization, particularly to the blastocyte stage, if desired after thawing the follicles, the male cells or the embryos.

The invention also has for its object a kit for the extemporaneous preparation of culture media as defined above according to the invention, particularly in the field of use of a process mentioned above, this kit comprising:

a composition in lyophilisate form, such as described above,
and, as the case may be, an aqueous solution containing elements conventionally used in the field of in vitro fertilization, or the culture of follicles, male cells or embryos, such as the elements defined above, particularly a commercial medium such as the Upgraded B9 medium of CCD.

The present invention will be further illustrated with the help of the detailed description which follows, of examples of culture media according to the invention.

As the aqueous solution as defined above, the Upgraded B9 CCD culture medium available commercially comprises principally the following compounds:

mineral salts: KCl, NaCl, $MgSO_4$, $NaHCO_3$, $Na_2HPO_4$, $KH_2PO_4$, essential amino acids, as well as other amino acids such as glutamic acid, glycine, taurine, cystein and glutamine, oses and metabolic derivatives, such as glucose, pyruvate, lactate, acetate, vitamins, particularly vitamins of the B group and vitamin C, purine and pyrimidine bases, antibiotics: penicillin G, streptomycin.

Formula No. 1

In this formula, the Upgraded B9 CCD culture medium corresponding to the aqueous solution defined above, if desired with added human insulin (particularly recombinant insulin in the amount of 5 mg/L, based on 1 mg=25 U), is completed with the lyophilisate containing:

hydrocortisone hemisuccinate ($7 \times 10^{-7}$ M, or 350 µg/L), recombinant human growth factors: EGF (50 µg/L), TGFα (25 µg/L), HGF (50 µg/L), GM-CSF (1.25 µg/L), GDF-9 (5 µg/L), NAD/NADH (1 mg/L) and NADP/NADPH (1 mg/L).

Formula No. 2

In this formula, the Upgraded B9 CCD culture medium, containing if desired human insulin, is completed by the lyophilisate containing:

hydrocortisone hemisuccinate ($7 \times 10^{-7}$ M, or 350 µg/L), recombinant human growth factors: EGF (50 µg/L), TGFα (25 µg/L), HGF (50 µg/L), GM-CSF (1.25 µg/L), GDF-9 (5 µg/L), IGF-1 (12.5 µg/L), IGF-2 (12.5 µg/L), and NAD/NADH (1 mg/L) and NADP/NADPH (1 mg/L).

A) Preparation of a Culture Medium for the Abovementioned Uses According to Formula No. 1

The culture medium must be prepared for immediate use by a mixture of two flasks:

flask A, which contains a solution of a volume of 10 ml and which contains the Upgraded B9 medium in which insulin is dissolved if desired;

flask B, which contains a lyophilisate and which contains hydrocortisone hemisuccinate and growth factors, NAD/NADH and NADP/NADPH.

At the instant of use, dissolve the lyophilisate from flask B in a small volume (about 0.5 ml) of the solution from flask A. Transfer the content of flask B thus dissolved into flask A. Homogenize. This operation hence dilutes to one tenth the initial concentration of the constituents of flask B.

Production of Flask A

In the case of the addition of insulin, it should be noted that in the crystalline condition, insulin molecules are interconnected by intermolecular forces which are broken only in acid medium. To be placed in aqueous condition, the insulin must therefore be dissolved at pH 3 (0.1 N HCl). The pH of the solution is then brought to 7.5 (0.1N NaOH); this operation must be carried out as rapidly as possible, so as to avoid alterations of the molecule. A slight precipitate can appear at pH5; it then redissolves.

A solution of 100 U/ml is then prepared. The solution of insulin is added to the Upgraded B9 medium, in the amount of 1.25 ml per liter, respectively. It is distributed into 10 ml flask which are closed. The solution is kept at +4° C. The analytic table for insulin, comprising among other things the activity and if desired the safety tests, should be included; the latter must be communicated by the supplier of the insulin.

Production of Flask B

An aqueous solution is prepared at the moment of use, containing hydrocortisone hemisuccinate and growth factors, is distributed into flasks of 1 ml, such that each flask contains 3.5 µg of hydrocortisone hemisuccinate, 500 µg of EGF, 250 ng of TGFα, 500 ng of HGF, 12.5 ng of GM-CSF, 50 µg of GDF-9, 10 µg of NAD/NADH and 10 µg of NADP/NADPH. The flasks are immediately lyophilized. The lyophilizate is held at +4° C.

Production Conditions

All the operations are carried out with previously sterilized materials and in sterile medium.

B) Preparation of a Culture Medium for the Abovementioned Uses According to Formula No. 2

IGF-1 and IGF-2 are added to the initial solution containing other constituents in flask B, to obtain 125 ng of each per flask, then the whole is lyophilized.

The production and preservation conditions are the same as those for the medium prepared according to formula No. 1.

C) Preparation of a Medium Containing Hydrocortisone and Growth Factors

In a first step, an experimental lot of medium containing glucocorticoid and growth factors was prepared. This culture medium was constituted by Upgraded B9 medium completed only with human insulin, hydrocortisone hemisuccinate, EGF, TGFα and human IGF-1.

To make up a 10 ml flask of Upgraded B9 medium, called flask A, we have used:

12.5 µl of an aqueous solution of human insulin of 100 U/ml. This solution was contained in a 10 ml flask, here called flask B. The safety tests (virus and prions) were first carried out.

a flask of lyophilizate of a capacity of 1.2 ml, here called flask C, containing hydrocortisone hemisuccinate (3.5 µg) and human recombinant growth and differentiation factors EGF (500 µg), TGFα (250 ng), and IGF-1 (125 ng). For the preparation of this flask, hydrocortisone hemisuccinate (1.4 mg), EGF (200 µg), TGFα (100 µg), and IGF-1 (50 µg) were dissolved in 400 ml of a secured human albumin aqueous solution (1 g/L). This solution was passed through a 0.2 µm filter, then distributed into 393 flasks of 5 ml, in the quantity of 1 ml per flask. These latter were lyophilized. All these operations were carried out in sterile medium.

What is claimed is:

1. A method for culturing biological material in vitro, the biological material being selected from the group consisting of follicles in the course of development for maturation of oocytes contained in said follicles, cells of a male germinal line to be matured, oocytes to be fertilized by a spermatozoa, and embryos to be cultured, said method comprising culturing said biological material in a culture composition comprising at least two growth factors in combination with at least one glucocorticoid compound, and, optionally with at least one co-enzyme of energy metabolism, optionally after thawing of the follicles, cells or embryos, wherein said at least two growth factors are selected from the group consisting of:
hepatic growth factors,
transformation growth factors α,
granulocyte and macrophage colony stimulation factor,
epidermal growth factor,
growth and differentiation factor (GDF), and
insulin-like growth factors.

2. The method according to claim 1, wherein said composition is present in the form of a reconstituted lyophilizate.

3. The method according to claim 2, wherein said reconstituted lyophilizate contains:
said at least two growth factors,
a hydrocortisone hemisucciante, and
NAD/NADH and NADP/NADPH.

4. The method according to claim 1, wherein said composition further comprises at least one element selected from the group consisting of human and bovine serum albumin, mineral salts, glucose, pyruvate, lactate, amino acids for biosynthesis of proteins, purine and pyrimidine bases for biosynthesis of nucleic acids, phospholipids, cholesterol, B vitamins and vitamin C.

5. A method for culturing biological material in vitro, the biological material being selected from the group consisting of follicles in the course of development for maturation of oocytes contained in said follicles, cells of a male germinal line to be matured, oocytes to be fertilized by a spermatozoa, and embryos to b cultured, said method comprising culturing said biological material in a culture composition comprising at least three growth factors in combination with at least one glucocorticoid compound, and, optionally with at least one co-enzyme of energy metabolism, optionally after thawing of the follicles, cells or embryos.

6. A method for culturing biological material in vitro, the biological material being selected from the group consisting of follicles in the course of development for maturation of oocytes contained in said follicles, cells of a male germinal line to be matured, oocytes to be fertilized by a spermatozoa, and embryos to be cultured, said method comprising culturing said biological material in a culture composition comprising at least two growth factors in combination with at least one glucocorticoid compound, and, optionally with at least one co-enzyme of energy metabolism, optionally after thawing of the follicles, cells or embryos,
    wherein said composition has nanomolar concentrations of said growth factors.

7. A method for culturing biological material in vitro, the biological material being selected from the group consisting of follicles in the course of development for maturation of oocytes contained in said follicles, cells of a male germinal line to be matured, oocytes to be fertilized by a spermatozoa, and embryos to be cultured, said method comprising culturing said biological material in a culture composition comprising at least two growth factors in combination with at least one glucocorticoid compound, and, optionally with at least one co-enzyme of energy metabolism, optionally after thawing of the follicles, cells or embryos,
    wherein the concentration of growth factors in said composition are comprised between about 0.25 $\mu$g/L and about 60 $\mu$g/L.

8. A method for culturing biological material in vitro, the biological material being selected from the group consisting of follicles in the course of development for maturation of oocytes contained in said follicles, cells of a male germinal line to be matured, oocytes to be fertilized by a spermatozoa, and embryos to be cultured, said method comprising culturing said biological material in a culture composition comprising at least two growth factors in combination with at least one glucocorticoid compound, and, optionally with at least one co-enzyme of energy metabolism, optionally after thawing of the follicles, cells or embryos,
    wherein the glucocorticoid compound is in water soluble form.

9. A method for culturing biological material in vitro, the biological material being selected from the group consisting of follicles in the course of development for maturation of oocytes contained in said follicles, cells of a male germinal line to be matured, oocytes to be fertilized by a spermatozoa, and embryos to be cultured, said method comprising culturing said biological material in a culture composition comprising at least two growth factors in combination with hydrocortisone in salt form, and, optionally with at least one co-enzyme of energy metabolism, optionally after thawing of the follicles, cells or embryos.

10. A method for culturing embryos in vitro, said method comprising culturing said embryos in a culture composition comprising at least two growth factors in combination with at least one glucocorticoid compound, and, optionally with at least one co-enzyme of energy metabolism, optionally after thawing of the embryos, wherein said culturing is effected.

11. A method for culturing human female follicles in the course of development for maturation of oocytes contained in said follicles, said method comprising culturing said follicles in a culture composition comprising at least two growth factors in combination with at least one glucocorticoid compound, and, optionally with at least one co-enzyme of energy metabolism, optionally after thawing of the follicles,
    wherein said culturing step comprises in vitro fertilization of human female follicles for about 3 days to about 6 days.

12. A method for culturing cell of a male germinal line to be matured, said method comprising culturing said biological material in a culture composition comprising at least two growth factors in combination with at least one glucocorticoid compound, and, optionally with at least one co-enzyme of energy metabolism, optionally after thawing of the cells, and wherein said culturing step comprises in vitro culturing of said cells, for about 3 days to a out 4 days.

13. A method for culturing oocytes to be fertilized by a spermatozoa, said method comprising culturing said oocytes in a culture composition comprising at least two growth factors in combination with at least one glucocorticoid compound, and, optionally with at least one co-enzyme of energy metabolism, and wherein said culturing step comprises in vitro culturing of the oocytes together with spermatozoa for about 2 days to about 6 days.

* * * * *